(12) United States Patent  
Ono et al.

(10) Patent No.: US 12,405,214 B2  
(45) Date of Patent: Sep. 2, 2025

(54) OPTICAL INSPECTION APPARATUS AND OPTICAL INSPECTION METHOD

(71) Applicant: Shimadzu Corporation, Kyoto (JP)

(72) Inventors: Takashi Ono, Kyoto (JP); Masahiro Ihara, Kyoto (JP); Hiromasa Maruno, Kyoto (JP); Satoshi Matsuoka, Kyoto (JP); Eri Matsutani, Kyoto (JP); Yusuke Koga, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 160 days.

(21) Appl. No.: 18/276,082

(22) PCT Filed: Dec. 8, 2021

(86) PCT No.: PCT/JP2021/045161  
§ 371 (c)(1),  
(2) Date: Aug. 7, 2023

(87) PCT Pub. No.: WO2022/201658  
PCT Pub. Date: Sep. 29, 2022

(65) Prior Publication Data  
US 2023/0417662 A1 Dec. 28, 2023

(30) Foreign Application Priority Data  
Mar. 26, 2021 (JP) .................. 2021-053836

(51) Int. Cl.  
*G01N 21/35* (2014.01)  
*G01N 21/3563* (2014.01)

(52) U.S. Cl.  
CPC . *G01N 21/3563* (2013.01); *G01N 2021/3595* (2013.01); *G01N 2201/021* (2013.01)

(58) Field of Classification Search  
CPC ....... G01N 21/3563; G01N 2021/3595; G01N 2201/021  
See application file for complete search history.

(56) References Cited

U.S. PATENT DOCUMENTS 10,520,405 B2    12/2019  Im  
2013/0118905 A1   5/2013  Morimoto et al.  
(Continued)

FOREIGN PATENT DOCUMENTS

CN    110646334 A    1/2020  
JP    2001-296240 A   10/2001  
(Continued)

OTHER PUBLICATIONS

First Office Action dated Feb. 6, 2024 issued for the corresponding Japanese Patent Application No. 2023-508464.  
(Continued)

*Primary Examiner* — Hugh Maupin  
(74) *Attorney, Agent, or Firm* — Muir Patent Law, PLLC

(57) ABSTRACT

One mode of an optical inspection apparatus according to the present invention is an optical inspection apparatus for optically inspecting an object, the optical inspection apparatus including: a biasing section (20) configured to apply, to a group of objects (23A) on a stage, a force for moving the group of objects away with respect to the stage (22); a catching section (24) including an adhesion portion (241) to which an object in the group of objects moved from the stage adheres; and an analysis section (3) configured to optically analyze the object caught by the catching section. This makes it possible to efficiently and satisfactorily perform optical analysis of individual microplastics by eliminating manual work of picking up the microplastics one by one.

11 Claims, 5 Drawing Sheets

(56) References Cited

U.S. PATENT DOCUMENTS

| | | | |
|---|---|---|---|
| 2021/0215584 A1* | 7/2021 | Carter | B01D 69/02 |
| 2021/0260501 A1* | 8/2021 | Lu | B01D 21/02 |
| 2023/0041820 A1* | 2/2023 | De Franceschi | G01N 33/442 |
| 2023/0314314 A1* | 10/2023 | Michel | G02B 27/0006 |
| | | | 250/341.1 |

FOREIGN PATENT DOCUMENTS

| | | |
|---|---|---|
| KR | 10-2013277 B1 | 8/2019 |
| WO | 2011/149032 A1 | 12/2011 |
| WO | 2013/114430 A1 | 8/2013 |

OTHER PUBLICATIONS

Primpke et al. "Reference database design for the automated analysis of microplastic samples based on Fourier transform infrared (FTIR) spectroscopy", Analytical and Bioanalytical Chemistry (Analytical and Bioanalytical Chemistry), vol. 410, 2018, pp. 5131-5141.

Written Opinion (ISA237) for PCT application No. PCT/JP2021/045161 dated Mar. 1, 2022.

Extended European Search Report dated Aug. 20, 2024 issued for the corresponding European Patent Application No. 21933251.7.

\* cited by examiner

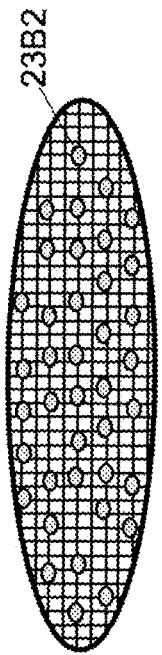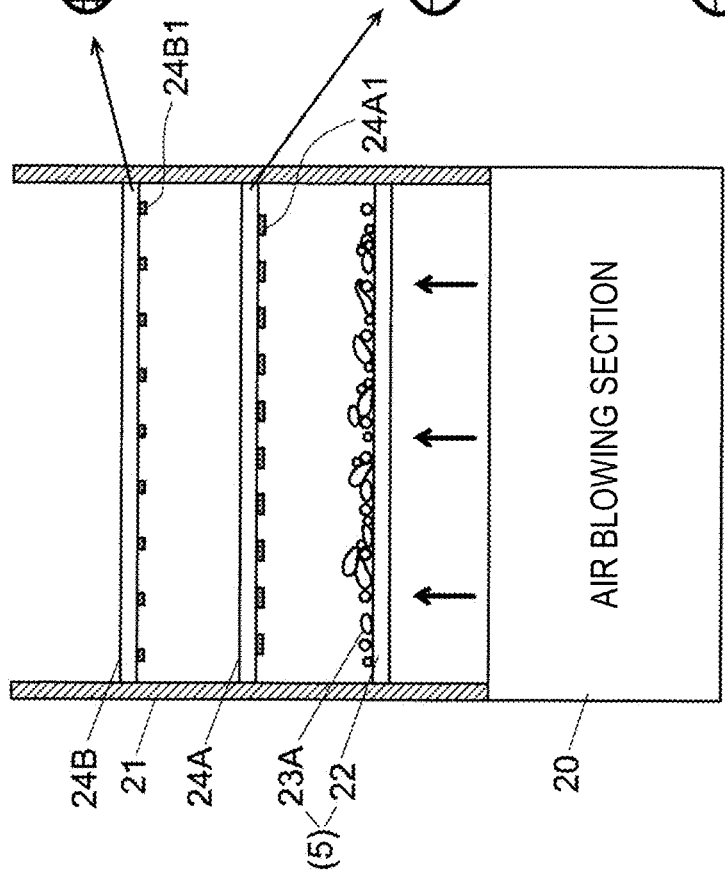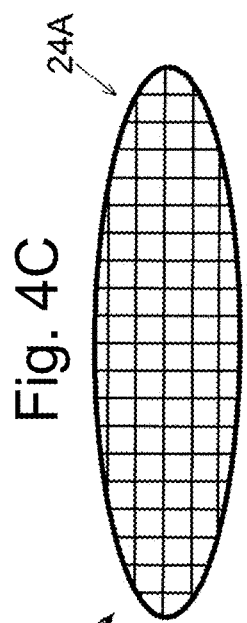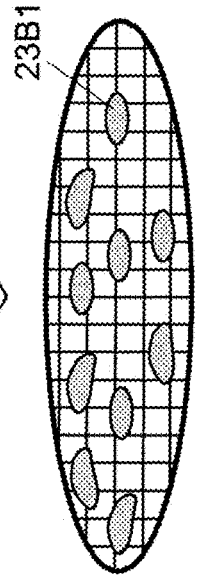

OPTICAL INSPECTION APPARATUS AND OPTICAL INSPECTION METHOD

TECHNICAL FIELD

The present invention relates to an optical inspection apparatus and method for optically inspecting a sample, and particularly relates to an optical inspection apparatus and method suitable for inspecting a large number of minute/fine samples such as microplastics.

BACKGROUND ART

In recent years, environmental pollution due to plastic waste has become a serious global issue. In particular, there is a growing concern that plastics having a size of 5 mm or less, which are called microplastics, adversely affect ecosystems in rivers and oceans, affecting human health by the food chain as well. For this reason, research for the purpose of large-scale distribution investigation and identification of a source of microplastics has been actively conducted in various places in the world.

At present, for component analysis of microplastics, an optical analysis method by a Fourier transform infrared spectrophotometer (FTIR), an infrared microscope using the FTIR, or the like is widely used (see Non Patent Literature 1).

CITATION LIST

Non Patent Literature

Non Patent Literature 1: Primpke (Sebastian Primpke) and 3 others, "Reference database design for the automated analysis of microplastic samples based on Fourier transform infrared (FTIR) spectroscopy (Reference database design for the automated analysis of microplastic samples based on Fourier transform infrared (FTIR) spectroscopy)", Analytical and Bioanalytical Chemistry (Analytical and Bioanalytical Chemistry), Vol. 410, 2018, pp. 5131-5141

SUMMARY OF INVENTION

Technical Problem

When a lightweight substance such as microplastics is sampled, small microplastic pieces are likely to be scattered in an overlapping state with each other. This makes optical analysis for measuring light absorption or transmission difficult to be performed in an accurate manner.

In such a case, an operator may manually pick up pieces while observing the microplastics with a microscope, and separates individual pieces from each other. This work requires a large amount of labor and time, making it difficult to increase the throughput of the inspection.

The present invention has been made to solve such problems, and a main object of the present invention is to provide an optical inspection apparatus and an optical inspection method capable of easily performing highly accurate inspection of microplastics or the like.

Solution to Problem

One mode of an optical inspection apparatus according to the present invention, which has been made to solve the above problems, is an optical inspection apparatus for optically inspecting an object, the optical inspection apparatus including:
 a biasing section configured to apply, to a group of objects on a stage, a force for moving the group of objects away with respect to the stage;
 a catching section including an adhesion portion to which an object in the group of objects moved from the stage adheres; and
 an analysis section configured to optically analyze the object caught by the catching section.

Another mode of the optical inspection apparatus according to the present invention is an optical inspection apparatus for optically inspecting an object, the optical inspection apparatus including:
 a biasing section configured to apply, to a group of objects on a stage, a force for moving the group of objects away with respect to the stage;
 a catching section configured to independently catch an object in the group of objects moved from the stage; and
 an analysis section configured to optically analyze the object caught by the catching section.

One mode of an optical inspection method according to the present invention is an optical inspection method for optically inspecting an object, the optical inspection method including:
 a sample creation step of applying, to a group of objects on a stage, a force for moving the group of objects away with respect to the stage, and adhering an object in the group of objects moved from the stage to an adhesion portion provided in a catching section; and
 an analysis step of optically analyzing the object caught by the catching section.

Advantageous Effects of Invention

In the above mode of the present invention, a group of objects prepared in a state of being placed on a stage is moved from the stage by the force applied by a biasing section. A plurality of objects may overlap each other on the stage in some cases. However, since each object moves (completely or to some extent) freely, the objects are dispersed separately from each other. Among the objects in the moved group of objects, the object that has come into contact with an adhesion portion of a catching section adheres to the adhesion portion. Since a new object does not adhere to a portion to which another object already adheres in the adhesion portion, overlapping of a plurality of objects is unlikely to occur in the catching section. That is, in the catching section, the plurality of objects are separated from each other in a state where the plurality of objects can be individually optically analyzed.

In this way, according to the above modes of the present invention, it is possible to prepare a sample in a state in which minute objects such as small pieces of microplastics in a sample such as a vial of water are appropriately dispersed and their positions are fixed without requiring labor and time such as manual work. As a result, for example, optical analysis of each piece of microplastic can be efficiently and satisfactorily performed. An additional advantage is that a series of steps from preparation to analysis of such a sample can be automated.

BRIEF DESCRIPTION OF DRAWINGS

FIGS. 3A and 3B are schematic configuration diagrams of the sample creation device in the optical inspection apparatus of the present embodiment, in which FIG. 3A is a state before a catching operation, and FIG. 3B is a state after the catching operation.

FIGS. 4A to 4C are schematic configuration diagrams illustrating a modification of the sample creation device.

DESCRIPTION OF EMBODIMENTS

"Objects" in an optical inspection apparatus and method according to the present invention can be, for example, minute/fine solids capable of dispersively floating in a liquid such as water. Typically, the objects are microplastics.

In addition, "optical analysis" in the optical inspection apparatus and method according to the present invention can include, for example, component analysis using spectrometry such as FTIR or X-ray fluorescence analysis, and analysis of the shape, size, color, and the like of the object based on optical observation using various microscopes such as a normal microscope, a phase contrast microscope, and an infrared microscope.

In addition, a "stage" in the optical inspection apparatus and method according to the present invention can include, for example, a plate-shaped member having a large number of openings such as a mesh filter, and a plate-shaped member made of a material having high water permeability/water absorbency such as filter paper.

Hereinafter, an embodiment of an optical inspection apparatus according to the present invention will be described with reference to the accompanying drawings.

Figure 1:
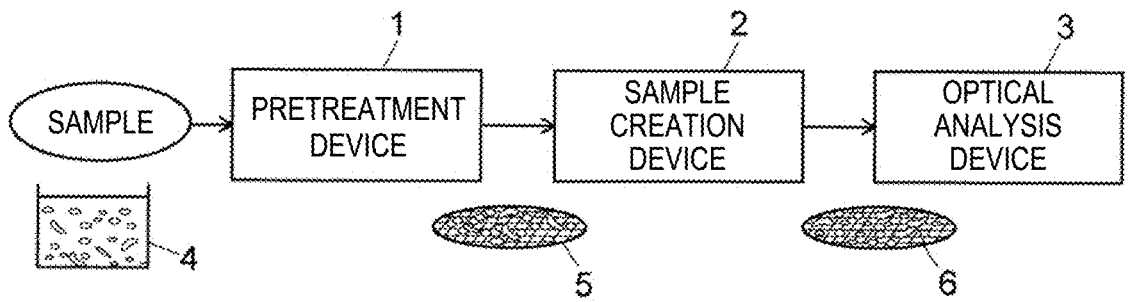
FIG. 1 is a schematic block configuration diagram of an optical inspection apparatus according to one embodiment of the present invention.

FIG. 1 is a schematic block configuration diagram of an optical inspection apparatus according to the present embodiment. This optical inspection apparatus performs inspection of microplastics contained in a liquid such as ocean water or river water, and includes a pretreatment device 1, a sample creation device 2, and an optical analysis device 3.

In order to analyze microplastics contained in a sample (water or the like) collected from the ocean, river, and the like by an analysis device of FTIR or the like, it is necessary to take out the microplastics from the sample as fully as possible to prepare the microplastics in a state where the microplastics can be analyzed. Therefore, typically, after pretreatment such as cleaning treatment for removing unnecessary organic substances adhering to surfaces of the microplastics present in the sample, gravity separation for separating the microplastics from other wastes, and the like is performed, the microplastics in the sample are collected by a metal mesh filter or the like.

To this end, the pretreatment device 1 performs the cleaning treatment using acid to remove dirt on the surfaces of the microplastics dispersed in a sample 4 such as ocean water containing the microplastics. After that, the microplastics are floated in the liquid by the gravity separation using sodium iodide (NaI). The liquid containing the gathering microplastics is filtered through the metal mesh filter to collect the microplastics. However, when there are a large number of microplastics, the microplastics (pieces) of various sizes and shapes collected on the metal mesh filter are in an overlapping state.

The sample creation device 2 receives a metal mesh filter 5 having a large number of plastic pieces (hereinafter, a large number of pieces are collectively referred to as "piece group") placed on the metal mesh filter 5. The pieces in this piece group have various sizes and shapes. In order to enable optical analysis of individual pieces, the sample creation device 2 prepares a sample in a state in which the pieces are separated from each other and are appropriately dispersed and fixed. A configuration and operation of the device for this end will be described in detail later.

The optical analysis device 3 receives a sample 6 in the state in which the pieces are appropriately dispersed and fixed, and discriminates the type of plastic of each piece by analyzing components contained in the piece. In parallel, information such as the size, shape, color, and the like of each piece is also collected. In this example, the optical analysis device 3 is a device in which the FTIR and a microscopic observation device are combined.

Figure 2A:
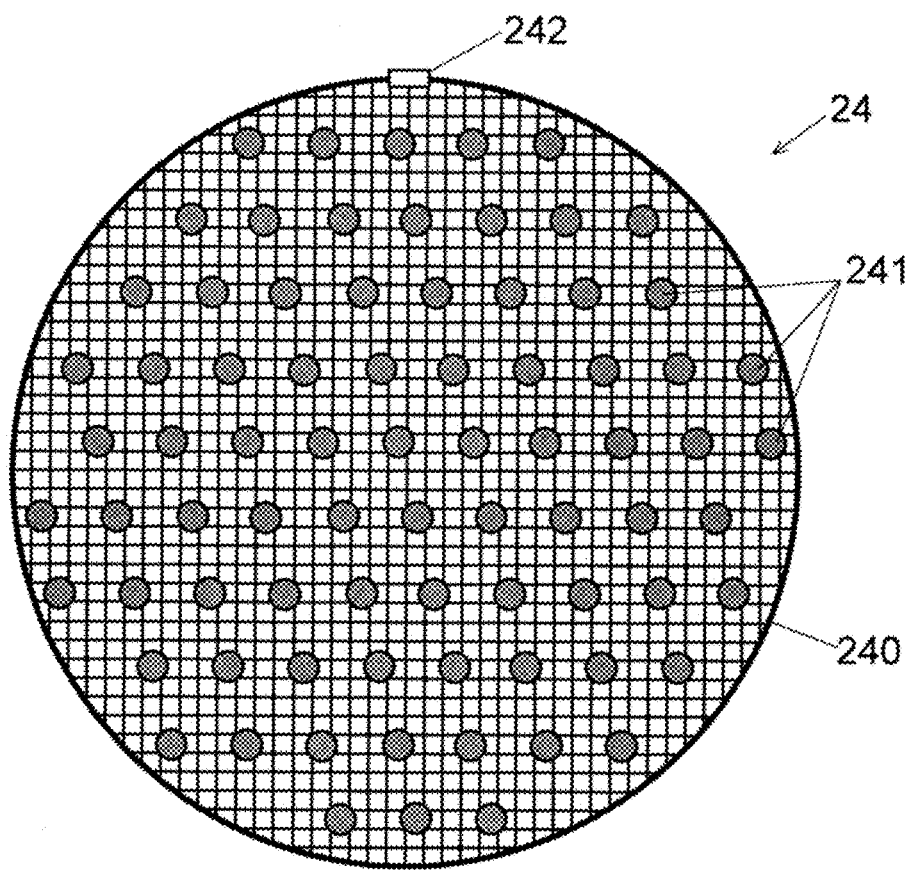
FIG. 2A is a top view and FIG. 2B is a front view of a catching mesh member used in a sample creation device in the optical inspection apparatus of the present embodiment.

Next, the configuration and operation of the sample creation device 2 will be described in detail. FIGS. 3A and 3B are schematic configuration diagrams of the sample creation device 2, in which FIG. 3A is a state before a catching operation, and FIG. 3B is a state after the catching operation. FIG. 2A is a top view and FIG. 2B is a front view of a catching mesh member.

As illustrated in FIG. 3A, the sample creation device 2 includes an air blowing section 20 which generates an upward air flow. The air blowing section 20 is not limited to a particular configuration. For example, one that generates an air flow using a rotating blade body such as a fan or a blower, one that generates an air flow using a compressed air source, or the like can be used. In any case, it is preferable that the air blowing section 20 can adjust a flow rate of the air flow and duration of the air blowing. As a result, it is possible to adjust an air volume or the like as appropriate according to the sizes and weights of the pieces as the objects, and adjust speed and spread when the pieces fly up. The air blowing section 20 may intermittently blow air.

A cylindrical casing 21 whose upper surface is opened and whose side is closed is disposed on the air blowing section 20 such that air blown from the air blowing section 20 travels upward without leaking to the side. Inside the casing 21, a metal mesh filter 22(5) is mounted substantially horizontally in a state in which the piece group including a large number of pieces 23A is placed on an upper surface so as to be spaced apart from the air blowing section 20 by a predetermined distance above the air blowing section 20. Furthermore, a catching mesh member 24 is set substantially horizontally above the metal mesh filter 22 so as to be spaced apart from the metal mesh filter 22 by a predetermined distance.

Figure 2B:
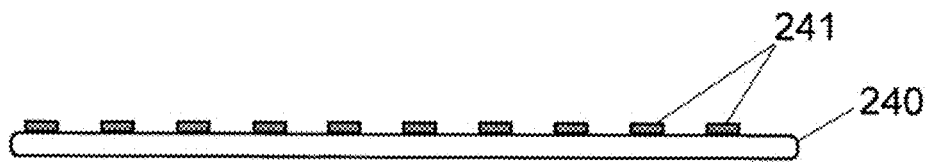
Figure 3A:
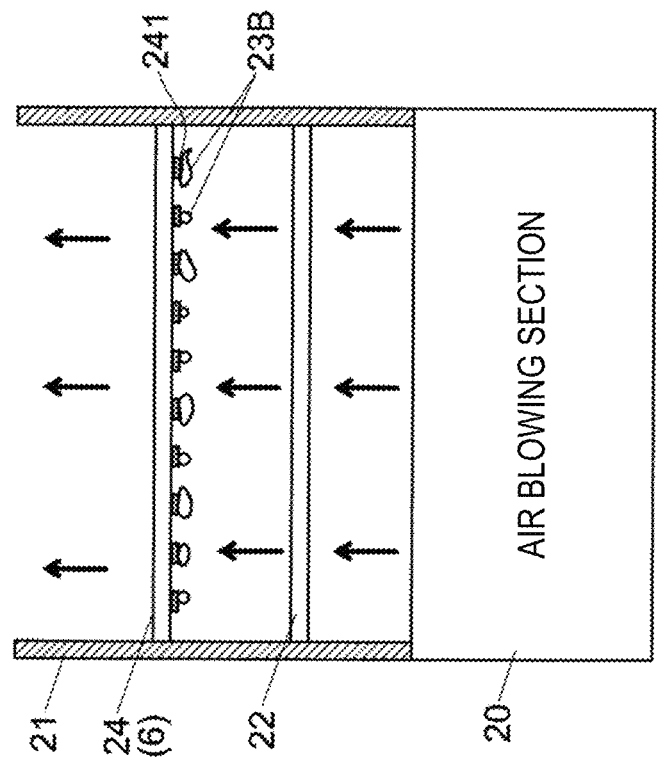
Figure 3B:
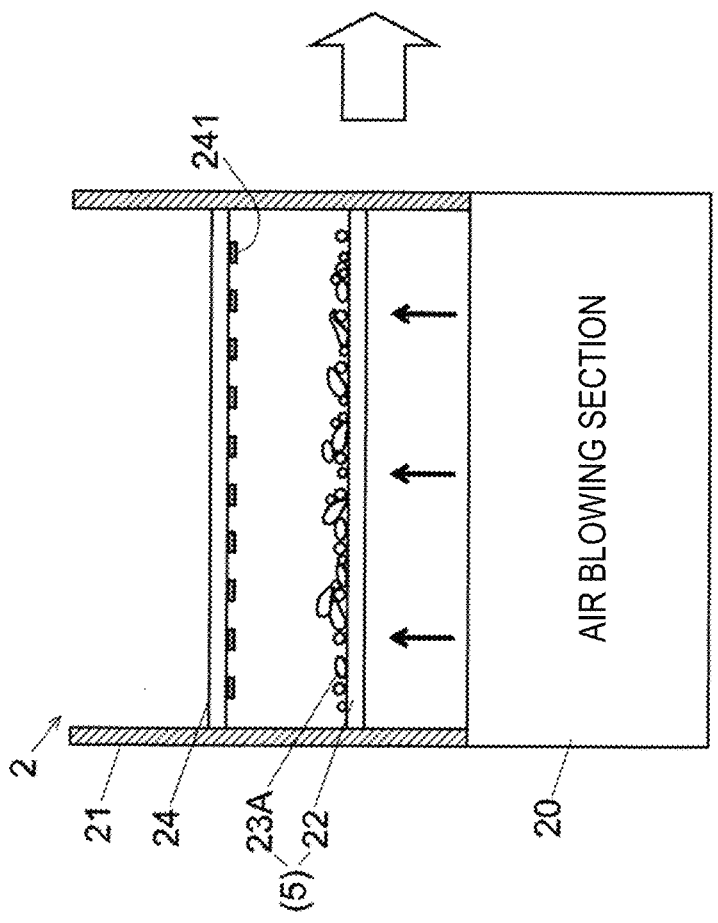

As illustrated in FIGS. 2A and 2B, in the catching mesh member 24, a plurality of adhesive portions 241 are provided according to a predetermined pattern on one surface of a main body portion 240 having a predetermined opening size (opening degree) similar to that of the metal mesh filter 22. The adhesive portion 241 is for fixing each piece. The type and material of a member of the adhesive portion 241 are not particularly limited, but it is preferable that the member does not interfere with component analysis by the FTIR. For this purpose, it is preferable to use an inorganic adhesive that is easily discriminated from an organic component. However, even when an organic adhesive agent is used, a spectrum of plastic contained in the piece as the object can be accurately obtained by performing correction processing such as subtracting a spectrum of components contained in the adhesive agent as long as the spectrum of components is known. Therefore, there is substantially no problem unless at least an adhesive agent made of the same material as the plastic is used for the adhesive portion 241.

In the example illustrated in FIGS. 2A and 2B, the shape of one adhesive portion 241 is substantially circular in top view, and the plurality of adhesive portions 241 are provided according to a pattern in which adjacent ones are disposed at substantially constant intervals. Although the shape of each adhesive portion 241 and the disposing pattern of the plurality of adhesive portions 241 are not limited to this configuration, it is preferable to match them with the sizes and shapes of the pieces to be caught. In addition, the opening degree of the main body portion 240 of the catching mesh member 24 may also be selected according to the dimensions of the pieces to be caught.

In addition, as illustrated in FIG. 2A, a reference marker 242 is provided on an outer peripheral edge of the catching mesh member 24. The reference marker 242 indicates a reference position of the plurality of adhesive portions 241. For example, discriminators such as consecutive numbers can be given to the plurality of adhesive portions 241 in one catching mesh member 24 with reference to this position. For example, as illustrated in FIG. 2A, in a state where the catching mesh member 24 is placed such that the reference marker 242 is on the top, respective rows of the adhesive portions 241 are designated as A, B, C, . . . in order from the top, and the adhesive portions 241 are numbered as 1, 2, 3, . . . in order from the left in each row. As a result, numbers A1, A2, A3, A4, A5, B1, B2, . . . can be given to all the adhesive portions 241 in the catching mesh member 24.

In the sample creation device 2, the air blowing section 20 is operated in the state illustrated in FIG. 3A to form an upward air flow. The air flow passes upward through openings of the metal mesh filter 22 and openings of the catching mesh member 24. The piece group placed on the metal mesh filter 22 is blown to fly up (that is, to float up) by the air flow from below. When the pieces included in the flying piece group come into contact with the adhesive portions 241 on the lower surface of the catching mesh member 24, the pieces stick to the adhesive portions 241 (see FIG. 3B). As a matter of course, no piece sticks to a portion where the adhesive portion 241 does not exist, and another piece does not stick to a portion to which one piece stick. Therefore, the pieces are separated from each other according to the disposing pattern of the adhesive portions 241, and are caught on one surface of the catching mesh member 24 in a state of being appropriately dispersed.

When almost all the pieces of the piece group on the metal mesh filter 22 are caught by the catching mesh member 24 by, for example, blowing air from the air blowing section 20 for a predetermined time, the air blowing is stopped and the catching mesh member 24 is taken out. When the number of pieces 23A on the metal mesh filter 22 is too large to be caught by one catching mesh member 24, almost all the pieces 23A on the metal mesh filter 22 may be caught by appropriately replacing the catching mesh member 24 with an unused one. In this way, the catching mesh member 24 in a state in which pieces 23B (the pieces adhering to the catching mesh member 24 are denoted by reference numeral 23B) stick to the adhesive portions 241 is transferred to the optical analysis device 3.

Figure 7:
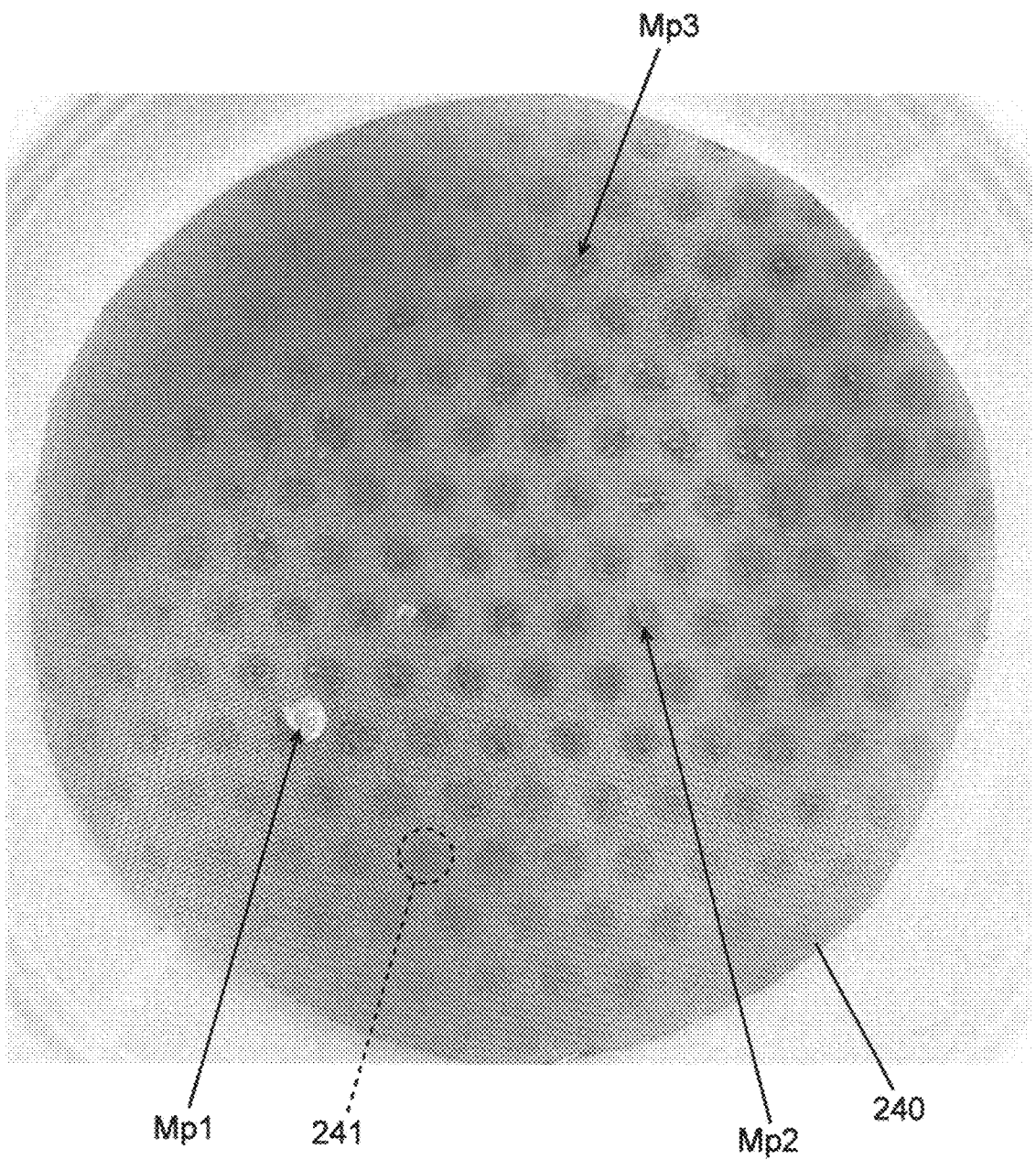
FIG. 7 is a photograph showing an example of a state in which microplastics are caught by the catching mesh member.

FIG. 7 is a photograph showing an example of a state in which a plurality of pieces are caught by the catching mesh member. In this example, there are three types of pieces (microplastics): a piece Mp1 having a size of about 2 to 5 mm, a piece Mp2 having a size of about 1 to 2 mm, and a piece Mp3 having a size of about 0.5 mm. The main body portion of the catching mesh member is 100 mesh (the number of openings in 25.4 mm). In addition, the adhesive portions 241 have a diameter of about 5 mm.

As illustrated in the drawing, since the adhesive portions 241 have a large diameter, a plurality of small pieces Mp3 stick to one adhesive portion 241. However, the pieces are separated from each other to an extent that the pieces can be individually analyzed by the FTIR. When the pieces are completely separated, the analysis accuracy is improved. However, even when the pieces are not completely separated from each other, that is, even when the pieces partly overlap, at least qualitative analysis can be performed. That is, here, the pieces included in the piece group are caught by the catching mesh member independently of each other.

In the optical analysis device 3, for example, the catching mesh member 24 (sample 6) to which a large number of pieces are fixed as described above is set on a sample stage as it is. The optical analysis device 3 acquires a microscopic observation image, and performs FTIR analysis on each piece. The catching mesh member 24 is set such that the reference marker 242 comes to a predetermined position (direction) at the time of setting the catching mesh member 24. Since the position where the adhesive portion 241 is provided in the two-dimensional plane is known, positioning for microscopic observation or FTIR analysis can be easily performed. That is, it is possible to perform rough positioning by targeting a range where the adhesive portion 241 exists, recognize the position where the piece actually exists within the range, and perform the FTIR analysis.

In addition, since the discrimination number is given to each adhesive portion 241 as described above, information such as a piece area obtained by the microscopic observation, information such as a spectrum obtained by the FTIR analysis, and a plastic discrimination result based on the information can be stored in association with the discrimination number. In addition, since the pieces caught by the catching mesh member 24 can be semipermanently fixed by using an adhesive agent as the adhesive portions 241, it is easy to convey (transport) the sample and store the sample for a long period of time. Therefore, when there is a doubt in the inspection result, the same sample can be reinspected or subjected to analysis/measurement by another method, so that more accurate and useful information can be acquired.

The conveyance of the sample among the pretreatment device 1, the sample creation device 2, and the optical analysis device 3 and the mounting of the sample on each device may be performed by an operator, but may also be automatically performed using a known handling mechanism or conveyance mechanism.

FIGS. 4A, 4B, and 4C are schematic configuration diagrams of a sample creation device 2 in an optical inspection apparatus according to another embodiment of the present invention. Structural components which are identical to those of the sample creation device illustrated in FIGS. 2A and 2B are denoted by the same numerals as used in FIGS. 2A and 2B, and detailed descriptions of those components will be omitted.

In this sample creation device, a plurality of catching mesh members having different opening sizes are disposed separately at predetermined intervals in a height direction. In this example, the number of catching mesh members 24A and 24B is two, but may be three or more. In that case, the interval between the adjacent catching mesh members may not be constant. In FIGS. 4B and 4C, illustration of adhesive portions 24A1 and 24B1 illustrated in FIG. 4A is omitted.

As illustrated in FIGS. 4A, 4B, and 4C, the opening size of the lower catching mesh member 24A is larger than the opening size of the upper catching mesh member 24B. In addition, the adhesive portions 24A1 of the lower catching mesh member 24A are larger than the adhesive portions 24B1 of the upper catching mesh member 24B. That is, the lower catching mesh member 24A has a coarser mesh. Therefore, in the piece group flying up by the air flow, pieces having a large size cannot pass through openings of the lower catching mesh member 24A, and most of the pieces stick to the adhesive portions 24A1 provided on the catching mesh member 24A. On the other hand, small pieces that have been able to pass through the openings of the lower catching mesh member 24A stick to the adhesive portions 24B1 provided on the upper catching mesh member 24B.

In this way, most of the pieces in the piece group can be classified according to their sizes and shapes, and then fixed in a state of being separated from each other although not completely separated (since some of the small pieces stick to the adhesive portions 24A1 provided on the lower catching mesh member 24A).

In the sample creation device 2 in the optical inspection apparatus according to the above embodiment, the air flow generated by the air blowing section 20 applies a force for causing the piece group to fly up to the piece group. However, the piece group can be moved by a different method.

Figure 5:
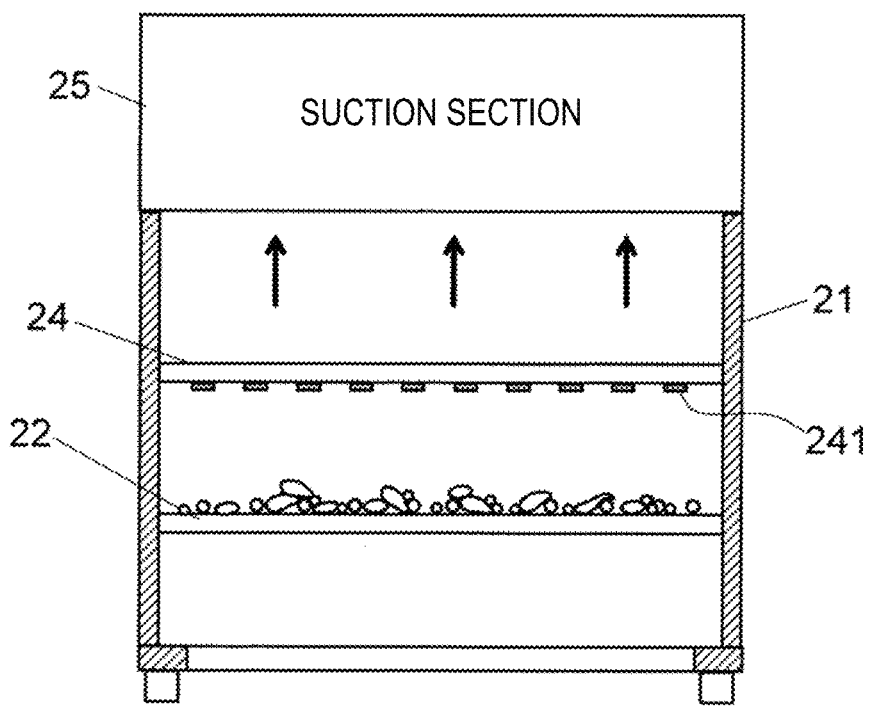
FIG. 5 is a schematic configuration diagram of a sample creation device according to another embodiment.

FIG. 5 is a schematic configuration diagram of a sample generation device according to another embodiment. In this example, a suction section 25 which is disposed above the catching mesh member 24 sucks air inside the casing 21 to generate an air flow from a lower side to an upper side. Of course, this enables an operation similar to that of the sample generation device in the above embodiment.

Figure 6:
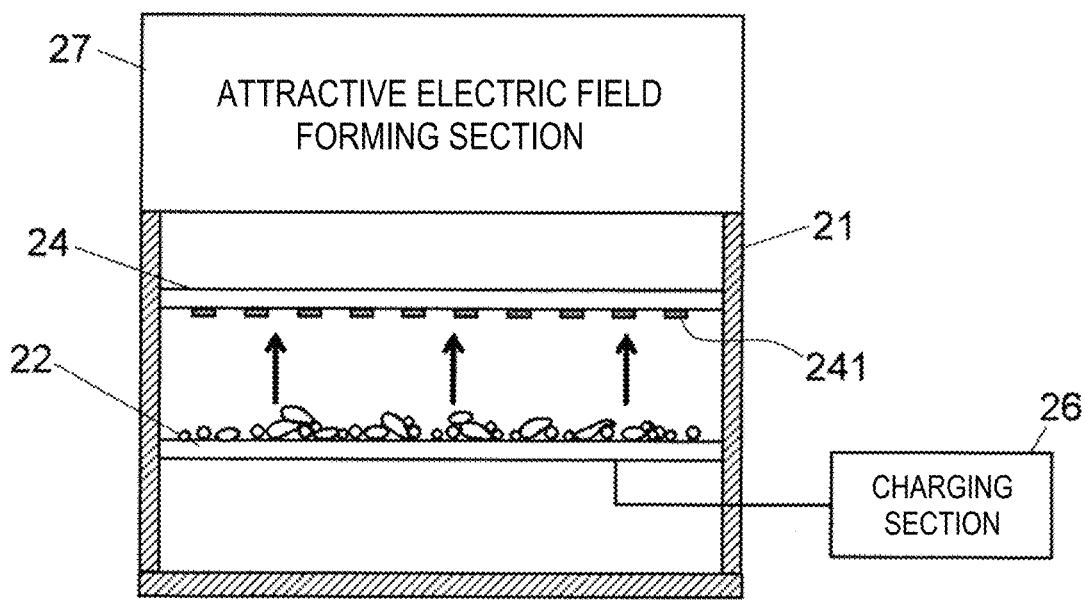
FIG. 6 is a schematic configuration diagram of a sample creation device according to another embodiment.

FIG. 6 is a schematic configuration diagram of a sample generation device according to yet another embodiment. In any of the above embodiments, the piece group is given a force by the air flow to be moved. However, in this embodiment, by using the fact that plastic is easily charged, the piece group is given a force by an electrostatic force to be moved.

In FIG. 6, a charging section 26 charges the pieces 23A on the metal mesh filter 22 to a predetermined polarity by applying a biased voltage to the pieces 23A. After that, an attractive electric field forming section 27 attracts the piece group by a voltage having a polarity opposite to the polarity of the charge of the pieces 23A. As a result, each piece 23A moves upward and sticks to the adhesive portion 241 of the catching mesh member 24.

However, the easiness of charging depends on the type of plastic, and the polarity of charging also varies depending on the type of plastic. Therefore, in order to catch all types of plastic pieces, it is preferable to perform the catching operation while changing the polarity and voltage value of the voltage generated in the charging section 26 and the attractive electric field forming section 27. In other words, it may be possible with this method to selectively catch a specific type of plastic piece. Therefore, classification according to the type of plastic is possible.

In addition, a mechanism for applying an impact from below to the metal mesh filter 22 on which the piece group is placed or vibrating the metal mesh filter 22 may be provided such that the pieces on the metal mesh filter 22 are flipped up or caused to fly up by the impact or vibration to be moved upward.

In addition, the above embodiments and modifications are merely examples of the present invention, and it is a matter of course that modifications, corrections, additions, and the like appropriately made within the scope of the gist of the present invention are included in the claims of the present application.

For example, the optical inspection apparatus according to the above embodiments uses the microplastics as the objects to be inspected, but the objects are not limited to the microplastics. For example, the optical inspection apparatus can be used in inspecting various materials such as minute/fine metal pieces, stones, and construction waste materials.

In addition, it is obvious that various optical analysis and observation methods including normal infrared spectrometry, ultraviolet-visible spectrometry, fluorescence spectrometry, Raman spectrometry, and X-ray fluorescence analysis in addition to the FTIR can be used as the optical analysis method.

Various Modes

It will be understood by those skilled in the art that the exemplary embodiments described above are specific examples of the following modes.

(Clause 1) One mode of an optical inspection apparatus according to the present invention is an optical inspection apparatus for optically inspecting an object, the optical inspection apparatus including:

a biasing section configured to apply, to a group of objects on a stage, a force for moving the group of objects away with respect to the stage;

a catching section including an adhesion portion to which an object in the group of objects moved from the stage adheres; and an analysis section configured to optically analyze the object caught by the catching section.

(Clause 9) In addition, one mode of an optical inspection method according to the present invention is an optical inspection method for optically inspecting an object, the optical inspection method including:

a sample creation step of applying, to a group of objects on a stage, a force for moving the group of objects away with respect to the stage, and adhering an object in the group of objects moved from the stage to an adhesion portion provided in a catching section; and an analysis step of optically analyzing the object caught by the catching section.

In accordance with the optical inspection apparatus according to Clause 1 and the optical inspection method according to Clause 9, it is possible to prepare a sample in a state in which minute objects such as microplastic pieces in a sample such as a vial of water are appropriately dispersed and their positions are fixed without requiring labor and time such as manual work. As a result, for example, optical analysis of each microplastic can be efficiently and satisfactorily performed. In addition, a series of steps from preparation to analysis of such a sample can be advantageously automated.

(Clause 2) In an optical inspection apparatus according to Clause 1, the catching section may be disposed above the stage in a vertical direction.

(Clause 10) Similarly, in an optical inspection method according to Clause 9, the catching section may be disposed above the stage in a vertical direction.

In accordance with the optical inspection apparatus according to Clause 2 and the optical inspection method according to Clause 10, another object that has come into contact with the object already adhering to the adhesion portion falls onto the stage by gravity. Therefore, it is possible to easily collect the object that has not adhered to the adhesion portion, and it is possible to adhere the collected object to the adhesion portion at another position by applying a force to the object again.

(Clause 3) In an optical inspection apparatus according to Clause 1 or 2, the stage may have a mesh shape, and the biasing section may include an air flow generating section configured to generate an air flow from a lower side to an upper side of the stage in a vertical direction.

(Clause 11) In addition, in an optical inspection method according to Clause 9 or 10, the stage may have a mesh shape in either case, and in the sample creation step, the group of objects may be moved upward from the stage by generating an air flow from a lower side to an upper side of the stage in a vertical direction.

In order to generate the air flow from the lower side to the upper side of the stage, the air flow may be blown from an air blowing section disposed below the stage, or may be formed by sucking air by a suction section disposed above the catching section.

In accordance with the optical inspection apparatus according to Clause 3 and the optical inspection method according to Clause 11, when the objects are relatively light like the microplastics, it is possible to make any objects fly up while dispersing the objects regardless of the physical characteristics or the like of the objects. As a result, the objects can be more reliably caught by the catching section. In addition, the apparatus can be configured at a relatively low cost.

(Clause 4) In an optical inspection apparatus according to any one of Clauses 1 to 3, a plurality of the adhesion portions may be provided in the catching section according to a predetermined pattern.

(Clause 12) In an optical inspection method according to any one of Clauses 9 to 11, a plurality of the adhesion portions may be provided in the catching section according to a predetermined pattern.

In the optical inspection apparatus according to Clause 4 and the optical inspection method according to Clause 12, the adhesion portions are provided at predetermined positions of the catching section. As a result, it becomes easy to grasp positions where the objects exist on the catching section, and thus, for example, when the analysis section performs another analysis after the optical analysis, traceability is improved.

(Clause 5) In an optical inspection apparatus according to any one of Clauses 1 to 4, the catching section may be provided with a reference marker indicating a reference position of the plurality of adhesion portions.

(Clause 13) In an optical inspection method according to any one of Clauses 9 to 12, the catching section may be provided with a reference marker indicating a reference position of the plurality of adhesion portions.

In accordance with the optical inspection apparatus according to Clause 5 and the optical inspection method according to Clause 13, it is possible to give discriminators such as consecutive numbers to the plurality of adhesion portions on the catching section with reference to the position of the reference marker, and manage analysis results of the respective pieces in association with the discriminators. In addition, the position of the reference marker can be used to perform positioning of the catching section at the time of analysis by the analysis section.

(Clause 6) In an optical inspection apparatus according to any one of Clauses 1 to 5, the catching section may include first and second mesh-shaped members disposed above the stage in a vertical direction so as to be separated from each other in a height direction, and the first and second mesh-shaped members may have opening sizes different from each other.

(Clause 14) In an optical inspection method according to any one of Clauses 9 to 13, the catching section may include first and second mesh-shaped members disposed above the stage in a vertical direction so as to be separated from each other in a height direction, and the first and second mesh-shaped members may have opening sizes different from each other.

In the optical inspection apparatus according to Clause 6 and the optical inspection method according to Clause 14, the mesh-shaped member having a large opening size is disposed at a relatively low position, that is, a position closer to the stage. As a result, in the object group moved upward from the stage, an object having a large size that cannot pass through the opening of the lower mesh-shaped member is caught by the lower mesh-shaped member, and an object having a small size that can pass through the opening of the lower mesh-shaped member is mainly caught by the upper mesh-shaped member. That is, in accordance with the optical inspection apparatus according to Clause 6 and the optical inspection method according to Clause 14, the objects are classified into quite a large number of groups according to their sizes and shapes, and the objects are caught by the first or second mesh-shaped member in the classified state.

(Clause 7) An optical inspection apparatus according to any one of Clauses 1 to 6 may further include a pretreatment section configured to perform at least one of cleaning treatment of the group of objects and separation treatment of the group of objects and impurities on a sample including the group of objects, wherein the stage may be a mesh-shaped filter which filters a treatment liquid including the sample after the treatment.

(Clause 15) In an optical inspection method according to any one of Clauses 9 to 14, a pretreatment step of performing at least one of cleaning treatment of the group of objects and separation treatment of the group of objects and impurities on a sample including the group of objects may be performed before the sample creation step, and the stage may be a mesh-shaped filter which filters a treatment liquid including the sample after the treatment.

In accordance with the optical inspection apparatus according to Clause 7 and the optical inspection method according to Clause 15, it is possible to analyze the group of objects having improved purity by removing dirt adhering to surfaces of the objects or eliminating impurities and the like. As a result, accurate information about each object can be acquired. In addition, for example, since it is possible to avoid analyzing unnecessary impurities and the like, the efficiency of the object inspection can be improved.

The optical inspection method according to the present invention can be used to inspect various inspection objects, and is particularly useful for inspecting microplastics.

(Clause 16) That is, in an optical inspection method according to any one of Clauses 9 to 15, the object to be inspected may be a microplastic.

(Clause 8) In an optical inspection apparatus according to any one of Clauses 1 to 7, the analysis section may be a Fourier transform infrared spectrophotometer.

(Clause 17) In an optical inspection method according to any one of Clauses 9 to 16, Fourier transform infrared spectroscopic analysis may be performed in the analysis step.

In accordance with the optical inspection device according to Clause 8 and the optical inspection method according to Clause 17, it is possible to efficiently inspect, for example, microplastics contained in ocean water, river water, and the like, and provide useful information for investigating a distribution situation of the microplastics and identifying a source of the microplastics.

(Clause 18) In addition, another mode of the optical inspection apparatus according to the present invention is an optical inspection apparatus for optically inspecting an object, the optical inspection apparatus including:

a biasing section configured to apply, to a group of objects on a stage, a force for moving the group of objects away with respect to the stage;

a catching section configured to independently catch an object in the group of objects moved from the stage; and an analysis section configured to optically analyze the object caught by the catching section.

The state of "independently catch each object" as used herein refers to a state in which at least the objects can be individually optically analyzed. Therefore, for example, in a case where the object is irradiated with light and transmitted light or reflected light for the light is measured, some of the plurality of objects may overlap each other as long as optical paths of the irradiation light and the transmitted light (reflected light) can be secured so that one object is not affected by other objects. Of course, the objects included in the object group may be in a state of being caught without overlapping or contacting each other. It is obvious that the optical inspection apparatus according to Clause 18 provides the same effects as those of the optical inspection apparatus according to Clause 1.

REFERENCE SIGNS LIST

1 . . . Pretreatment Device
2 . . . Sample Creation Device
20 . . . Air Blowing Section
21 . . . Casing
22 . . . Metal Mesh Filter
23A, 23B . . . Microplastic
24(5) . . . Catching Mesh Member
240 . . . Main Body Portion
241, 24A1, 24B1 . . . Adhesive Portion
242 . . . Reference Marker
25 . . . Suction Section
26 . . . Charging Section
27 . . . Attractive Electric Field Forming Section
3 . . . Optical Analysis Device

The invention claimed is:

1. An optical inspection apparatus for optically inspecting an object, the optical inspection apparatus comprising:
a biasing section configured to apply, to a group of objects on a stage, a force for moving the group of objects away with respect to the stage;
a catching section including an adhesion portion to which an object in the group of objects moved from the stage adheres, the adhesion portion being capable of holding the object while the force applied by the biasing section is canceled; and
an analysis section configured to optically analyze the object held by the adhesion portion,
wherein a plurality of the adhesion portions are provided in the catching section according to a predetermined pattern.

2. The optical inspection apparatus according to claim 1, wherein the catching section is disposed above the stage in a vertical direction.

3. The optical inspection apparatus according to claim 1, wherein the stage has a mesh shape, and wherein the biasing section includes an air flow generating section configured to generate an air flow from a lower side to an upper side of the stage in a vertical direction.

4. The optical inspection apparatus according to claim 1, wherein the catching section is provided with a reference marker indicating a reference position of a plurality of the adhesion portions.

5. The optical inspection apparatus according to claim 1, wherein
the catching section includes first and second mesh-shaped members disposed above the stage in a vertical direction so as to be separated from each other in a height direction, and
the first and second mesh-shaped members have opening sizes different from each other.

6. The optical inspection apparatus according to claim 1, further comprising:
a pretreatment section configured to perform at least one of cleaning treatment of the group of objects and separation treatment of the group of objects and impurities on a sample including the group of objects, wherein
the stage is a mesh-shaped filter which filters a treatment liquid including the sample after the treatment performed by the pretreatment section.

7. The optical inspection apparatus according to claim 1, wherein the analysis section is a Fourier transform infrared spectrophotometer.

8. An optical inspection method for optically inspecting an object, the optical inspection method comprising:
a sample creation step of applying, to a group of objects on a stage, a force for moving the group of objects away with respect to the stage, and adhering an object in the group of objects moved from the stage to an adhesion portion which is capable of holding the object while the force is canceled; and
an analysis step of optically analyzing the object caught by a catching section,
wherein a plurality of the adhesion portions are provided in the catching section according to a predetermined pattern.

9. The optical inspection method according to claim 8, wherein the object is a microplastic.

10. The optical inspection method according to claim 8, wherein Fourier transform infrared spectroscopic analysis is performed in the analysis step.

11. An optical inspection apparatus for optically inspecting an object, the optical inspection apparatus comprising:
a biasing section configured to apply, to a group of objects on a stage, a force for moving the group of objects away with respect to the stage;
a catching section including an adhesion portion to which an object in the group of objects moved from the stage adheres, the adhesion portion being capable of holding the object while the force applied by the biasing section is canceled; and an analysis section configured to optically analyze the object held by the adhesion portion, wherein the catching section is disposed above the stage in a vertical direction.

\* \* \* \* \*